United States Patent

Ruess et al.

Patent Number: 6,117,892
Date of Patent: Sep. 12, 2000

[54] CROP PROTECTION PRODUCTS

[75] Inventors: Wilhelm Ruess, Pfeffingen, Switzerland; Gertrude Knauf-Beiter, Müllheim, Germany; Ruth Beatrice Küng, Allschwil, Switzerland; Helmut Kessmann, Lörrach, Germany

[73] Assignee: Novartis Finance Corp., N.Y.

[21] Appl. No.: 09/282,124

[22] Filed: Mar. 31, 1999

Related U.S. Application Data

[62] Division of application No. 08/875,015, Jul. 16, 1997, Pat. No. 5,945,437, and a continuation of application No. PCT/EP96/00096, Jan. 11, 1996.

[30] Foreign Application Priority Data

Jan. 23, 1995 [CH] Switzerland ............... 179/95

[51] Int. Cl.⁷ ............ A01N 43/64; A01N 43/82
[52] U.S. Cl. ............... 514/361; 514/383
[58] Field of Search ............... 514/361, 383

[56] References Cited

U.S. PATENT DOCUMENTS

| | | | |
|---|---|---|---|
| 4,079,062 | 3/1978 | Van Reet et al. | 260/308 R |
| 4,151,299 | 4/1979 | Hubele | 424/309 |
| 5,190,928 | 3/1993 | Schurter et al. | 514/63 |
| 7,800,469 | 7/1998 | Ruess | 514/237.5 |

FOREIGN PATENT DOCUMENTS 1176799  1/1970  United Kingdom.

OTHER PUBLICATIONS

Worthing et al, The Pesticide Manual, 9$^{th}$ Ed. (1991) pp. 278, 654 & 724 & 725.
Gil et al., Pest. Biochem. & Physiol., vol. 7, 183–193 (1977).
Chem. Abst., vol. 85, No. 17, Abst. 117936, Oct. 25, 1976.
Worthing et al., The Pesticide Manual, 9th ed., 554–555 (1991).
Chem. Abst., vol. 87, No. 9, Abst. 64015, Aug. 29, 1922.

*Primary Examiner*—Allen J. Robinson
*Attorney, Agent, or Firm*—Gabriel Lopez

[57] ABSTRACT

Plant-protecting mixtures of active ingredients having a synergistically increased action, wherein component I is a compound having a plant-immunizing action of the formula I

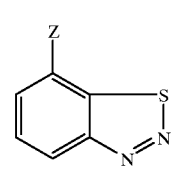

in which Z is CN, COOH or a salt thereof, CO—OC$_1$–C$_4$alkyl or CO—SC$_1$–C$_4$alkyl;

and wherein component II is a compound selected from the group consisting of propiconazole, difenoconazole, penconazole, fenpropimorph, fenpropidine, cyprodinil, metalaxyl, R-metalaxyl and pyroquilon.

14 Claims, No Drawings

CROP PROTECTION PRODUCTS

This is a Division of Ser. No. 08/875,015, Jul. 16, 1997, U.S. Pat. No. 5,945,437, and a continuation of PCT/EP96/00096, filed Jan. 11, 1996.

The present invention relates to novel crop-protecting mixtures of active ingredients having a synergistically increased action, this mixture comprising at least one compound having a plant-immunizing action and at least one compound having a microbicidal action, and to methods for using such mixtures in crop protection, in particular for controlling and preventing the incidence of disease.

Component I is a plant-immunizing compound of the formula I

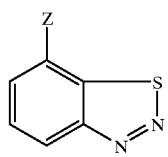

I in which
Z is CN, COOH or a salt thereof, CO—O$C_1$–$C_4$alkyl or CO—S$C_1$–$C_4$alkyl;

component II is a compound selected from the group consisting of
A) 1-[2-(2,4-dichlorophenyl)-4-propyl-1,3-dioxolan-2-ylmethyl]-1H-1,2,4-triazole, ("propiconazole"), (reference: GB-1 522 657);
B) 1-{2-[2-chloro-4-(4-chlorophenoxy)phenyl]-4-methyl-1,3-dioxolan-2-ylmethyl}-1H-1,2,4-triazole, ("difenoconazole"), (reference: GB-2 098 607);
C) 1-[2-(2,4-dichlorophenyl)pentyl-1H-1,2,4-triazole, ("penconazole"), (reference: GB-1 589 852);
D) cis-4-[3-(4-tert-butylphenyl)-2-methylpropyl]-2,6-dimethylmorpholine, ("fenpropimorph"), (reference: DE 2 752 135);
E) 1-[3-(4-tert-butylphenyl)-2-methylpropyl]piperidine, ("fenpropidin"), (reference: DE 2 752 135);
F) 4-cyclopropyl-6-methyl-N-phenyl-2-pyrimidinamine ("cyprodinil") (reference: EP-A-310 550);
G) (RS)-N-(2,6-dimethylphenyl)-N-(methoxyacetyl) alanine methyl ester ("metalaxyl"), (reference: GB-1 500 581);
H) (R)-N-(2,6-dimethylphenyl)-N-(methoxyacetyl)alanine methyl ester ("R-metalaxyl"), (reference: GB-1 500 581);
J) 1,2,5,6-tetrahydro-4H-pyrrolo[3,2,1-ij]quinolin-4-one ("pyroquilon"), (reference: GB-1 394 373).

The invention also relates to salts and metal complexes of the compounds I and II Preferred compounds among those of the formula I are compounds in which Z is COOH (compound IA) or a salt thereof, CN (compound IB), COO$CH_3$ (compound IC) or COS$CH_3$ (compound ID).

Preferred salts are alkali metal and alkaline earth metal salts, in particular Li, Na, K, Mg or Ca salts, furthermore organic salts, in particular those of salt-forming amines, for example trimethylamine, triethylamine, N,N-dimethylaniline, pyridine, triethanolamine, morpholine.

Very particularly preferred is the compound of the formula I in which Z is CO—S$CH_3$ (compound ID).

It has been disclosed that compounds of the formula I activate the plant's latent, own defence system against the effects of pathogenic microbes and thus are capable of protecting the plant against pathogens (EP-A-313 512).

At low rates of application, these compounds are not directly active against the harmful organisms, but cause immunization of the healthy plant against diseases.

The disadvantage of controlling plant diseases using compounds of the formula I is that the action is frequently insufficient at low rates of application.

Surprisingly, it has now been found that compounds of the formula I, when mixed in certain ratios with one of the conventional microbicides IIA to IIJ, have a synergistically increased action. Such mixtures are suitable for controlling plant diseases by, on the one hand, strengthening the plant by activating its own defence system and, on the other hand, additionally controlling the pathogens directly.

In comparison with the conventional methods of controlling plant diseases, unexpectedly low amounts of active ingredients are required.

A particular advantage of the mixtures according to the invention is furthermore the fact that the build-up of resistance, of plant diseases, is prevented effectively by the completely different mechanisms of action of components I and II. The synergistically increased action of mixtures of components I and II is shown, for example, by the lower rates of application, the longer duration of action and the higher overall yields than was to be expected from the total of the actions of the individual components.

The present invention also relates to a method of protecting plants against plant diseases, in particular fungus infestation, by treating the plants, parts of plants or their environment with a component I and a component II in any order or simultaneously.

Advantageous mixing ratios of the two active ingredients are I:II=1:30 to 10:1, preferably I:II=1:20 to 2:1 and 1:10 to 1:1.

Particularly advantageous mixing ratios are
I:IIA=1:1 to 1:6
I:IIB=1:1 to 1:6
I:IIC=1:1 to 1:5
I:IID=1:1 to 1:10
I:IIE=1:1 to 1:10
I:IIF=1:20 to 1:10
I:IIG=10:1 to 1:10
I:IIH=10:1 to 1:5
I:IIJ=10:1 to 1:10

The mixtures according to the invention of active ingredients I+II have very advantageous properties for protecting plants against the incidence of disease.

The present mixtures of active ingredients are capable of containing or destroying the microorganisms which occur on plants or parts of plants (fruits, flowers, foliage, stalks, tubers, roots) of a variety of crops of useful plants, and even parts of plants which are formed at a later point in time remain unharmed by such microorganisms. They can also be employed as seed-dressing agents for treatment of plant propagation material, in particular seed (fruits, tubers, kernels) and nursery plants (for example rice) as a protection against fungal infections and against soil-borne phytopathogenic fungi. The mixtures of active ingredients according to the invention are distinguished by particularly good toleration by plants and favourable ecological properties.

The mixtures of active ingredients are effective against the phytopathogenic fungi of the following classes: Ascomycetes (for example Venturi a, Podosphaera, Erysiphe, Monilinia, Mycosphaerella, Uncinula); Basidiomycetes (for example the genera Hemileia, Rhizoctonia, Puccinia); *Fungi*

*imperfecti* (for example Botrytis, Helminthosporium, Rhynchosporium, Fusarium, Septoria, Cercospora, Alternaria, Pyricularia and, in particular, *Pseudocercosporella herpotrichoides*); Oomycetes (for example Phytophthora, Peronospora, Bremia, Pythium, Plasmopara).

Target crops for the fields of indication disclosed in the present publication are, within the scope of the invention, for example the following plant species: cereals (wheat, barley, rye, oats, rice, sorghum and related species); beet (sugar and fodder beet); pomaceous fruit, stone fruit and soft fruit (apples, pears, plums, peaches, almonds, cherries, strawberries, raspberries and blackberries); leguminous plants (beans, lentils, peas, soya beans); oil crops (oilseed rape, mustard, poppies, olives, sunflowers, coconut, castor, cocoa, groundnuts); cucurbits (pumpkins, cucumbers, melons); fibre plants (cotton, flax, hemp, jute); citrus fruit (oranges, lemons, grapefruit, tangerines); vegetables (spinach, lettuce, asparagus, cabbages, carrots, onions, tomatoes, potatoes, bell peppers); the laurel family (avocado, Cinnamonum, camphor), or plants such as maize, tobacco, nuts, coffee, sugar cane, tea, grapevines, hops, the plantain family and latex plants, and also ornamentals (flowers, shrubs, deciduous trees and conifers). This enumeration is not by way of limitation.

The mixtures of active ingredients according to the invention are particularly advantageous for the following applications:

I+IIA, I+IIB, I+IID, I+IIE: in cereals, very particularly in wheat and barley;

I+IIG, I+IIH, very particularly I+IIH: in potatoes, grapevines, lawns, hops, tobacco and vegetables;

I+IIJ: in rice.

The mixtures of active ingredients of the formulae I and II are conventionally used in the form of compositions. The active ingredients of the formulae I and II can be applied to the area or plant to be treated either simultaneously or in succession on the same day, if desired together with other carriers conventionally used in the art of formulation, surfactants or other additives which aid application.

Suitable carriers and additives can be solid or liquid and are the substances expediently used in the art of formulation, for example natural or regenerated mineral materials, solvents, dispersants, wetting agents, adhesives, thickeners, binders or fertilizers.

A preferred method of applying a mixture of active ingredients comprising in each case at least one of these active ingredients I and II is application to the aerial parts of the plant, especially the foliage (foliar application). Number and rates of application depend on the biological and climatic environment of the pathogen. Alternatively, the active ingredients can reach the plant from the soil or water via the root system (systemic action) by drenching the locus of the plant with a liquid preparation (for example in rice growing) or incorporating the substances into the soil in solid form, for example in the form of granules (soil application). The compounds of the formulae I and II can also be applied to seed kernels for the purposes of seed treatment (coating), either by soaking the roots or kernels in succession with a liquid preparation of an active ingredient or by coating them with a moist or dry preparation which already comprises the combination. In addition, other types of application to plants are possible in specific cases, for example the targeted treatment of buds or fruit-bearing parts of the plant.

The compounds of the combination are employed as pure active ingredients or, preferably, together with the auxiliaries conventionally used in the art of formulation and are therefore processed in a known manner to give, for example, emulsion concentrates, spreadable pastes, ready-to-spray or ready-to-dilute solutions, dilute emulsions, wettable powders, soluble powders, dusts, granules, or encapsulations, for example in polymeric materials. The methods of application, such as spraying, atomizing, dusting, scattering, brushing on or pouring, and the type of composition are selected to suit the intended aims and prevailing circumstances. Advantageous rates of application of the mixture of active ingredients are generally 50 g to 2 kg of a.i./ha, in particular 100 g to 1000 g of a.i./ha, particularly preferably 150 g to 700 g of a.i./ha. For the treatment of seed, the rates of application are 0.5 g–1000 g, preferably 5 g–100 g of a.i. per 100 kg of seed.

The formulations are prepared in a known manner, for example by intimately mixing and/or grinding the active ingredients with extenders, for example solvents, solid carriers and, if desired, surface-active compounds (surfactants).

Suitable solvents are: aromatic hydrocarbons, preferably the fractions $C_8$ to $C_{12}$, for example xylene mixtures or substituted naphthalenes, phthalic esters, such as dibutyl phthalate or dioctyl phthalate, aliphatic hydrocarbons, such as cyclohexane or paraffins, alcohols and glycols and also their ethers and esters, such as ethanol, ethylene glycol, ethylene glycol monomethyl ether or ethylene glycol monoethyl ether, ketones, such as cyclohexanone, strongly polar solvents, such as N-methyl-2-pyrrolidone, dimethyl sulfoxide or dimethylformamide, and free or epoxidized vegetable oils, such as epoxidized coconut oil or soya oil; or water.

Solid carriers which are used for example for dusts and dispersible powders are, as a rule, ground natural minerals, such as calcite, talc, kaolin, montmorillonite or attapulgite. To improve the physical properties, it is also possible to add highly-disperse silica or highly-disperse absorptive polymers. Suitable particulate adsorptive carriers for granules are porous types, for example pumice, brick grit, sepiolite or bentonite, and suitable non-sorptive carrier materials are, for example, calcite or sand. Moreover, a large number of pregranulated materials of inorganic or organic nature can be used, such as, in particular, dolomite or comminuted plant residues.

Depending on the nature of the active ingredients of the formulae I and II to be formulated, suitable surface-active compounds are non-ionic, cationic and/or anionic surfactants having good emulsifying, dispersing and wetting properties. Surfactants are also to be understood as meaning mixtures of surfactants.

Particularly advantageous additives which aid application are, furthermore, natural or synthetic phospholipids from the series of the cephalins and lecithins, for example phosphatidylethanolamine, phosphatidylserine, phosphatidylglycerine, lysolecithin.

As a rule, the agrochemical preparations comprise 0.1 to 99%, in particular 0.1 to 95%, of active ingredients of the formulae I and II, 99.9 to 1%, in particular 99.9 to 5%, of a solid or liquid additive and 0 to 25%, in particular 0.1 to 25%, of a surfactant.

While concentrates are more preferred as commercially available goods, the end consumer uses, as a rule, dilute compositions.

Such compositions are part of the present invention.

The examples which follow are intended to illustrate the invention, "active ingredient" being to be understood as meaning a mixture of compound I and compound II in a certain mixing ratio.

| Formulation examples | | | |
|---|---|---|---|
| Wettable powders | a) | b) | c) |
| Active ingredient [I:II = 1:3(a), 1:2(b), 1:1(c)] | 25% | 50% | 75% |
| Sodium lignosulfonate | 5% | 5% | — |
| Sodium laurylsulfate | 3% | — | 5% |
| Sodium diisobutylnaphthalene-sulfonate | — | 6% | 10% |
| Octylphenol polyethylene glycol ether (7–8 mol of ethylene oxide) | — | 2% | — |
| Highly disperse silica | 5% | 10% | 10% |
| Kaolin | 62% | 27% | — |

The active ingredient is mixed thoroughly with the additives and the mixture is ground thoroughly in a suitable mill. This gives wettable powders which can be diluted with water to give suspensions of any desired concentration.

| Emulsion concentrate | |
|---|---|
| Active ingredient (I:II = 1:6) | 10% |
| Octylphenol polyethylene glycol ether (4–5 mol of ethylene oxide) | 3% |
| Calcium dodecylbenzenesulfonate | 3% |
| Castor oil polyglycol ether (35 mol of ethylene oxide) | 4% |
| Cyclohexanone | 30% |
| Xylene mixture | 50% |

Emulsions of any desired dilution which can be employed in crop protection can be prepared from this concentrate by dilution with water.

| Dusts | a) | b) | c) |
|---|---|---|---|
| Active ingredient [I:II = 1:4 (a); 1:5 (b) and 1:1 (c)] | 5% | 6% | 4% |
| Talc | 95% | — | — |
| Kaolin | — | 94% | — |
| Rock meal | — | — | 96% |

Ready-to-use dusts are obtained by mixing the active ingredient with the carrier and grinding the mixture in a suitable mill. Such powders can also be used for dry seed treatment.

| Extruder granules | |
|---|---|
| Active ingredient (I:II = 2:1) | 15% |
| Sodium lignosulfonate | 2% |
| Carboxymethylcellulose | 1% |
| Kaolin | 82% |

The active ingredient is mixed with the additives, ground and moistened with water. This mixture is extruded and subsequently dried in a stream of air.

| Coated granules | |
|---|---|
| Active ingredient (I:II = 1:10) | 8% |
| Polyethylene glycol (MW 200) | 3% |
| Kaolin | 89% |

(MW = molecular weight)

In a mixer, the finely ground active ingredient is applied uniformly to the kaolin which has been moistened with polyethylene glycol. This gives dust-free coated granules.

| Suspension concentrate | |
|---|---|
| Active ingredient (I:II = 1:7) | 40% |
| Propylene glycol | 10% |
| Nonylphenol polyethylene glycol ether (15 mol of ethylene oxide) | 6% |
| Sodium lignosulfonate | 10% |
| Carboxymethylcellulose | 1% |
| Silicone oil (in the form of a 75% aqueous emulsion) | 1% |
| Water | 32% |

The finely ground active ingredient is mixed intimately with the additives. This gives a suspension concentrate from which suspensions of any desired dilution can be prepared by dilution with water. Such dilutions can be used for treating live plants and plant propagation material by means of spraying, pouring-on or immersion and for protecting them against microbial infection.

Biological Examples

A synergistic effect is present if the action of the combination of active ingredients exceeds the total of the actions of the individual components.

The expected action E for a given combination of active ingredients can be described by the so-called COLBY formula and can be calculated as follows (COLBY, S. R. "Calculating synergistic and antagonistic responses of herbicide combination". Weeds, Vol. 15, pages 20–22; 1967):

ppm=milligrams of active ingredient (=a.i.) per litre of spray mixture

X=% action caused by active ingredient I at a rate of application of p ppm of active ingredient Y=% action caused by active ingredient II at a rate of q ppm of active ingredient E=expected action of active ingredients I+II at a rate of application of p+q ppm of active ingredient (additive action), then Colby's formula reads $$E = X + Y - \frac{X \cdot Y}{100}.$$

If the actually observed action (O) exceeds the expected action (E), the action of the combination is superadditive, i.e. there is a synergistic effect. O/E=factor of synergism (FS).

In the examples which follow, the infestation of the untreated plant is considered 100%, which corresponds to an action of 0%.

A) Examples in which

Component I: Compound ID (thiomethyl benzothiadiazole-7-carboxylate)

Component II: Compound IIA (propiconazole)

Example A1: Action against *Puccinia recondita* in Wheat 7-day-old wheat plants are sprayed to drip point with a spray mixture prepared from a formulated active ingredient, or combination of active ingredients. After 4 days, the treated plants are infected with a conidia suspension of the fungus, and the treated plants are subsequently incubated for 2 days at a relative atmospheric humidity of 90–100% and 20° C. 10 days post-infection, the fungus infestation is assessed. The following results are obtained:

| Exp. | mg of a.i. per litre | | | % action found | calculated | FS |
|---|---|---|---|---|---|---|
| No. | a.i. ID | a.i. IIA | I:II | O | E | O/E |
| 0 | — | — | | 0 (control) | | |
| 1 | 100 | — | | 51 | | |
| 2 | — | 5 | | 10 | | |
| 3 | 100 | 5 | 20:1 | 79 | 56 | 1.4 |

Example A2: Action against *Erysiphe graminis* in Wheat in the Open (experimental site: Les Barges, Dalais, Switzerland In a field trial (10 m²), winter wheat cv. "Bernina" in the growth phase is sprayed with a spray mixture prepared with a wettable powder of the active ingredient. Infection is naturally. 10 days post-infection, the fungus infestation is assessed. The following results are obtained:

| Exp. | g of a.i. per ha | | | % action found | calculated | FS |
|---|---|---|---|---|---|---|
| No. | a.i. ID | a.i. IIA | I:II | O | E | O/E |
| 0 | — | — | | 0 (control) | | |
| 1 | 5 | — | | 29 | | |
| 2 | — | 50 | | 2 | | |
| 3 | — | 100 | | 31 | | |
| 4 | 5 | 50 | 1:10 | 49 | 32 | 1.5 |
| 5 | 5 | 100 | 1:20 | 59 | 51 | 1.2 |

Example A3: Action against *Mycosphaerella fijiensis* in Bananas (experimental site: Ombu Farm, Prov. Limon, Costa Rica)

40 banana plants in a 300 m² plot are sprayed at 17–19 day intervals with a spray mixture prepared with the wettable powder of the active ingredient; in total 6 times. Infection is naturally. For evaluation, the leaf area infested with fungus is measured. The following results are obtained:

| Exp. | g of a.i. per ha | | | % action found | calculated | FS |
|---|---|---|---|---|---|---|
| No. | a.i. ID | a.i. IIA | I:II | O | E | O/E |
| 0 | — | — | | 0 (control) | | |
| 1 | 50 | — | | 19 | | |
| 2 | — | 50 | | 26 | | |
| 3 | 50 | 50 | 1:1 | 46 | 40 | 1.15 |

Similarly good results are obtained using mixtures of one of the compounds IA, IB or IC with the compound IIa.

B) Examples in which

Component I: Compound ID (thiomethyl benzothiadiazole-7-carboxylate)

Component II: Compound IIF (cyprodinil)

Example B1: Action against *Erysiphe graminis* in Wheat in the Open (experimental site: Whittlesford, England)

In a field trial (10 m²), winter wheat cv. "Kanzler" in growth phase 31–32 is sprayed with a spray mixture prepared with a wettable powder of the active ingredient. Infection was naturally. The following results are obtained:

| Exp. | g of a.i. per ha | | | % action found | calculated | FS |
|---|---|---|---|---|---|---|
| No. | a.i. ID | a.i. IIF | I:II | O | E | O/E |
| 0 | — | — | | 0 (control) | | |
| 1 | 25 | — | | 32 | | |
| 2 | 50 | — | | 63 | | |
| 3 | — | 750 | | 38 | | |
| 4 | 25 | 750 | 1:30 | 75 | 58 | 1.3 |
| 5 | 50 | 750 | 1:15 | 88 | 77 | 1.1 |

Example B2: Action against *Alternaria solani* in Tomatoes in the Open (experimental site: Cikampek, Java, Indonesia Tomato plants on a 7 m² plot are sprayed at 7-day intervals with a spray mixture prepared with a wettable powder of the active ingredient; in total 9 times. Infection is naturally. For evaluation, the leaf area infested with the fungus is measured. The following results are obtained:

| Exp. | g of a.i. per ha | | | % action found | calculated | FS |
|---|---|---|---|---|---|---|
| No. | a.i. ID | a.i. IIF | I:II | O | E | O/E |
| 0 | — | — | | 0 (control) | | |
| 1 | 2.5 | — | | 32 | | |
| 2 | — | 12.5 | | 30 | | |
| 3 | — | 25 | | 51 | | |
| 4 | 2.5 | 12.5 | 1:5 | 79 | 53 | 1.5 |
| 5 | 2.5 | 25 | 1:10 | 80 | 67 | 1.2 |

Similarly good results are obtained using mixtures of one of the compounds IA, IB or IC with the compound IIF.

C) Examples in which

Component I: Compound ID (thiomethyl benzothiadiazole-7-carboxylate)

Component II: Compound IIG (metalaxyl)

Example C1: Action against *Phytophthora infestans* in Tomatoes

Tomato plants cv. "Roter Gnom" are sprayed to drip point with a spray mixture prepared with the formulated active ingredient, or combination of active ingredients. After 4 days, the treated plants are sprayed with a sporangia suspension of the fungus and subsequently incubated in a cabinet for 2 days at 18–20° C. and a relative atmospheric humidity of 90–100%. 5 days post-infection, the fungus infestation is assessed. The following results are obtained:

| Exp. | mg of a.i. per litre | | | % action found | calculated | FS |
|---|---|---|---|---|---|---|
| No. | a.i. ID | a.i. IIG | I:II | O | E | O/E |
| 0 | — | — | | 0 (control) | | |
| 1 | 5 | | | 14 | | |
| 2 | 25 | | | 36 | | |
| 3 | 100 | | | 61 | | |
| 4 | 500 | | | 72 | | |
| 5 | — | 0.1 | | 13 | | |
| 6 | | 1 | | 23 | | |
| 7 | | 10 | | 35 | | |
| 8 | | 50 | | 68 | | |
| 9 | 5 | 0.1 | 50:1 | 50 | 25 | 2.0 |
| 10 | 5 | 1 | 5:1 | 62 | 34 | 1.8 |
| 11 | 5 | 10 | 1:2 | 87 | 44 | 2.0 |
| 12 | 5 | 50 | 1:10 | 84 | 73 | 1.2 |
| 13 | 25 | 50 | 1:2 | 92 | 80 | 1.2 |
| 14 | 100 | 10 | 10:1 | 85 | 75 | 1.1 |
| 15 | 100 | 50 | 2:1 | 95 | 88 | 1.1 |
| 16 | 500 | 10 | 50:1 | 97 | 82 | 1.2 |

Similarly good results are obtained with mixtures of one of the compounds IA, IB or IC with the compound IIG.

Particularly good results with regard to the degradability of the active ingredient in the soil are achieved by mixtures of compound ID with compound IIH.

D) Examples in which

Component I: Compound IA=benzothiadiazole-7-carboxylic acid

Component II: Comound IIG (metalaxyl)

Example D1: Action against *Phytophthora infestants* in Tomatoes

The experiments are carried out as described for Example C1. The following results are obtained:

| Exp. | mg of a.i. per litre | | | % action found | calculated | FS |
|---|---|---|---|---|---|---|
| No. | a.i. IA | a.i. IIG | I:II | O | E | O/E |
| 0 | — | — | | 0 (control) | | |
| 1 | 0.1 | | | 0 | | |
| 2 | 0.5 | | | 9 | | |
| 3 | 1 | | | 22 | | |
| 4 | 5 | | | 45 | | |
| 5 | | 1 | | 13 | | |
| 6 | | 10 | | 33 | | |
| 7 | | 50 | | 63 | | |
| 8 | | 100 | | 83 | | |
| 9 | 0.1 | 1 | 1:10 | 36 | 13 | 2.8 |
| 10 | 0.5 | 1 | 1:2 | 29 | 21 | 1.4 |
| 11 | 1 | 1 | 1:1 | 57 | 32 | 1.8 |
| 12 | 1 | 10 | 1:10 | 79 | 48 | 1.6 |
| 13 | 5 | 1 | 5:1 | 61 | 52 | 1.2 |

Example D2: Action against *Pseudoperonospora cubensis* in Cucumbers

16–19-day-old cucumber plants ("Wisconsin") are sprayed to drip point with a spray mixture prepared with the formulated active ingredient, or combination of active ingredient, or combination of active ingredients. After 4 days, the treated plants are infected with sporangia of Pseudoperonospora cubensis (strain 365, Ciba; max. 5000 per ml), and the treated plants are subsequently incubated for 1–2 days at 18–20° C. and a relative atmospheric humidity of 70–90%. 10 days post-infection, the fungus infestation is assessed and compared with the infestation on untreated plants. The following results are obtained:

| Exp. | mg of a.i. per litre | | | % action found | calculated | FS |
|---|---|---|---|---|---|---|
| No. | a.i. IA | a.i. IIG | I:II | O | E | O/E |
| 0 | — | — | | 0 (control) | | |
| 1 | 0.05 | | | 0 | | |
| 2 | 0.5 | | | 6 | | |
| 3 | 5 | | | 66 | | |
| 4 | | 0.5 | | 31 | | |
| 5 | | 5 | | 66 | | |
| 6 | | 50 | | 91 | | |
| 7 | 0.05 | 0.5 | 1:10 | 66 | 31 | 2.1 |
| 8 | 0.05 | 5 | 1:100 | 83 | 66 | 1.3 |
| 9 | 0.5 | 0.5 | 1:1 | 83 | 35 | 2.4 |
| 10 | 0.5 | 5 | 1:10 | 83 | 68 | 1.2 |

E) Examples in which

Component I: Compound ID (thiomethyl benzothiadiazole-7-carboxylate)

Component II: Compound IIJ (pyroquilon)

Example E1: Action against *Pyricularia oryzae* in Rice in the Open (experimental site: Ono, Japan)

On a 12 m² plot, rice plants are sprayed with a spray mixture prepared with a wettable powder of the active ingredient. Infection is naturally. For evaluation, the leaf area infested with the fungus is measured 44 days post-application.

The following results are obtained:

| Exp. | kg of a.i. per ha | | | % action found | calculated | FS |
|---|---|---|---|---|---|---|
| No. | a.i. ID | a.i. IIJ | I:II | O | E | O/E |
| 0 | — | — | | 0 (control) | | |
| 1 | 0.25 | | | 22 | | |
| 2 | 0.5 | | | 50 | | |
| 3 | | 0.75 | | 46 | | |
| 4 | | 1.5 | | 82 | | |
| 5 | 0.25 | 0.75 | 1:3 | 80 | 58 | 1.4 |
| 6 | 0.5 | 0.75 | 1:1.5 | 85 | 73 | 1.2 |

Similarly good results are obtained with mixtures of one of the compounds IA, IB or IC with compound IIJ.

F) Examples in which

Component I: Compound IA (benzothiadiazole-7-carboxylic acid)

Component II: Compound IID (fenpropimorph)

Example F1: Action against *Cercospora nicotianae* in Tobacco Plants 6-week-old tobacco plants (cv. "Burley") are sprayed to drip point with a spray mixture prepared with the formulated active ingredient, or combination of active ingredients. After 4 days, the treated plants are infected with a spore suspension of Cercospora nicotianae (Ciba No. 295; max. 150,000 per ml), and the treated plants are subsequently incubated for 5 days at 20–22° C. and a relative atmospheric humidity of 70–90%. 10 days post-infection, the fungus infestation is assessed and compared with the infestation on untreated plants.

The following results are obtained:

| Exp. No. | kg of a.i. per ha | | | % action found | calculated | FS |
|---|---|---|---|---|---|---|
| | a.i. IA | a.i. IID | I:II | O | E | O/E |
| 0 | — | — | | 0 (control) | | |
| 1 | 0.2 | | | 0 | | |
| 2 | 0.6 | | | 3 | | |
| 3 | 2 | | | 69 | | |
| 4 | 6 | | | 79 | | |
| 5 | | 2 | | 13 | | |
| 6 | | 6 | | 23 | | |
| 7 | | 10 | | 42 | | |
| 8 | 0.2 | 2 | 1:10 | 52 | 13 | 4 |
| 9 | 0.2 | 6 | 1:30 | 61 | 23 | 2.7 |
| 10 | 0.6 | 2 | 1:3 | 71 | 16 | 4.4 |
| 11 | 6 | 6 | 1:1 | 100 | 83 | 1.2 |

G) Examples in which

Component I: Compound IA (benzothiadiazole-7-carboxylic acid)

Component II: Compound IIE (fenpropidine) Example G1: Action against *Puccinia recondita* in Wheat The experiments are carried out as described for Example A1. The following results are obtained:

| Exp. No. | kg of a.i. per ha | | | % action found | calculated | FS |
|---|---|---|---|---|---|---|
| | a.i. IA | a.i. IIE | I:II | O | E | O/E |
| 0 | — | — | | 0 (control) | | |
| 1 | 6 | | | 20 | | |
| 2 | 20 | | | 40 | | |
| 3 | | 20 | | 40 | | |
| 4 | | 60 | | 60 | | |
| 5 | 6 | 20 | 1:3 | 73 | 52 | 1.4 |
| 6 | 6 | 60 | 1:10 | 75 | 68 | 1.1 |

H) Examples in which

Component I: Compound IA (benzothiadiazole-7-carboxylic acid)

Component II: Compound IIB (difenoconazole)

Example H1: Action against *Cercospora nicotianae* in Tobacco Plants

The experiments are carried out as described for Example F1. The following results are obtained:

| Exp. No. | kg of a.i. per ha | | | % action found | calculated | FS |
|---|---|---|---|---|---|---|
| | a.i. IA | a.i. IIB | I:II | O | E | O/E |
| 0 | — | — | | 0 (control) | | |
| 1 | 2 | | | 69 | | |
| 2 | 6 | | | 79 | | |
| 3 | 20 | | | 100 | | |
| 4 | | 0.6 | | 3 | | |
| 5 | | 2 | | 23 | | |
| 6 | | 6 | | 32 | | |

-continued

| Exp. No. | kg of a.i. per ha | | | % action found | calculated | FS |
|---|---|---|---|---|---|---|
| | a.i. IA | a.i. IIB | I:II | O | E | O/E |
| 7 | 2 | 0.6 | 3:1 | 90 | 70 | 1.3 |
| 8 | 6 | 0.6 | 10:1 | 100 | 80 | 1.3 |

What is claimed is:

1. A composition which comprises a pesticidally effective amount of at least two, synergistically active components together with a suitable carrier material, wherein component I is a compound having a plant-immunizing action of the formula I

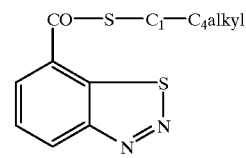

and component II is a compound selected from the group consisting of
  A) 1-[2-(2,4-dichlorophenyl)-4-propyl-1,3-dioxolan-2-ylmethyl]-1H-1,2,4-triazole;
  B) 1-{2-[2-chloro-4-(4-chlorophenoxy)phenyl]-4-methyl-1,3-dioxolan-2-ylmethyl}-1H-1,2,4-triazole; and
  C) 1-{2-(2,4-dichlorophenyl)pentyl-1H-1,2,4-triazole
wherein the weight ration I:II is 1:30 to 10:1.

2. A composition of claim 1 wherein the weight ratio of I:II is 1:20 to 10:1.

3. A composition of claim 2 wherein the weight ratio is 1:10 to 3:1.

4. A composition of claim 1 wherein $C_1$–$C_4$alkyl is methyl.

5. A composition of claim 1 wherein component II is 1-[2-(2,4-dichlorophenyl)-4-propyl-1,3-dioxolan-2-ylmethyl]-1H-1,2,4-triazole.

6. A composition of claim 1 wherein component II is 1-{2-[2-chloro-4-(4-chlorophenoxy)phenyl]-4-methyl-1,3-dioxolan-2-ylmethyl}-1H-1,2,4-triazole.

7. A composition of claim 1 wherein component II is 1-{2-(2,4-dichlorophenyl)pentyl-1H-1,2,4-triazole.

8. A method of protecting plants against plant diseases by treating the plants, parts of the plants, or their environment with a synergistically effective amount of a component I and a component II in any order or simultaneously, wherein component I is of the formula I

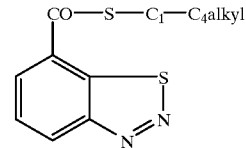

and component II is a compound selected from the group consisting of

A) 1-[2-(2,4-dichlorophenyl)-4-propyl-1,3-dioxolan-2-ylmethyl]-1H-1,2,4-triazole;
B) 1-{2-[2-chloro-4-(4-chlorophenoxy)phenyl]-4-methyl-1,3-dioxolan-2-ylmethyl}-1H-1,2,4-triazole; and
C) 1-{2-(2,4-dichlorophenyl)pentyl-1H-1,2,4-triazole wherein the weight ration I:II is 1:30 to 10:1.

9. A method of claim 8 wherein the weight ratio of I:II is 1:20 to 10:1.

10. A method of claim 8 wherein the weight ratio of I:II is 1:10 to 3:1.

11. A method of claim 8 wherein $C_1$–$C_4$ alkyl is methyl.

12. A method of claim 8 wherein component II is 1-[2-(2,4-dichlorophenyl)-4-propyl-1,3-dioxolan-2-ylmethy]-1H-1,2,4-triazole.

13. A method of claim 8 wherein component II is 1-{2-[2-chloro-4-(4-chlorophenoxy)phenyl]-4-methyl-1,3-dioxolan-2-ylmethyl}-1H-1,2,4-triazole.

14. A method of claim 8 wherein component II is 1-{2-(2,4-dichlorophenyl)pentyl-1H-1,2,4-triazole.

* * * * *